US008377465B2

(12) United States Patent
Drouillard

(10) Patent No.: US 8,377,465 B2
(45) Date of Patent: Feb. 19, 2013

(54) PRODUCT AND PROCESS FOR ELEVATING LIPID BLOOD LEVELS IN LIVESTOCK

(75) Inventor: James S. Drouillard, Olsbburg, KS (US)

(73) Assignee: Kansas State University Research Foundation, Manhattan, KS (US)

(*) Notice: Subject to any disclaimer, the term of this patent is extended or adjusted under 35 U.S.C. 154(b) by 1964 days.

(21) Appl. No.: 11/056,953

(22) Filed: Feb. 11, 2005

(65) Prior Publication Data

US 2006/0182827 A1 Aug. 17, 2006

(51) Int. Cl.
*A23K 1/18* (2006.01)

(52) U.S. Cl. ......... 424/438; 424/768; 426/520; 426/807

(58) Field of Classification Search ........................ None
See application file for complete search history.

(56) References Cited

U.S. PATENT DOCUMENTS

| | | | |
|---|---|---|---|
| 4,431,675 A * | 2/1984 | Schroeder et al. | 426/69 |
| 4,731,249 A * | 3/1988 | Findley | 426/69 |
| 5,110,592 A * | 5/1992 | Stitt | 424/768 |
| 5,459,162 A | 10/1995 | Saxton | |
| 5,482,729 A | 1/1996 | McKenzie et al. | |
| 5,639,794 A | 6/1997 | Emerson et al. | |
| 5,824,707 A | 10/1998 | Saxton | |
| 5,948,667 A | 9/1999 | Cheng et al. | |
| 6,137,032 A | 10/2000 | Cheng et al. | |
| 6,143,335 A * | 11/2000 | McKenzie | 426/72 |
| 6,726,941 B2 | 4/2004 | Ethington, Jr. et al. | |
| 2003/0175403 A1 | 9/2003 | Gurin | |
| 2003/0199556 A1 | 10/2003 | Krzyzaniak et al. | |
| 2004/0018288 A1* | 1/2004 | Westberg | 426/523 |
| 2004/0058003 A1 | 3/2004 | Rosenberg et al. | |

OTHER PUBLICATIONS

Barber, M. D., J. A. Ross, T. Preston, A. Shenkin, and K. C. H. Fearon. 1999. Fish oil-enriched nutritional supplement attenuates progression of the acute-phase response in weight-losing patients with advanced pancreatic cancer. J. Nutr. 129:1120-1125.
Besler, H. T., and R. F. Grimble. 1995. Comparison of the modulatory influence of maize and olive oils and butter on metabolic responses to endotoxin in rats. Clinical Science. 88:59-66.
Blatteis, C. M., J. R. Hales, A. A. Fawcett, and T. A. Mashburn Jr. 1988. Fever and regional blood flows in wethers and parturient ewes. J. Appl. Physiol. 65(1):165-172.
Calder, P.C. 1998. Immunoregulatory and anti-inflammatory effects of $n$-3 polyunsaturated fatty acids. Brazilian Journal of Medical and Biological Research 31:467-490.
Calder, P. C. 1997. n-3 Polyunsaturated fatty acids and cytokine production in health and disease. Ann. Nutr. Metab. 41:203-234.
Calder, P. C. 1998a. Fat chance of immunomodulation. Immunology Today 19(6):244-247.

(Continued)

*Primary Examiner* — Daniel Sullivan
*Assistant Examiner* — Barbara Frazier
(74) *Attorney, Agent, or Firm* — Hovey Williams LLP

(57) ABSTRACT

The present invention provides feed or food products for consumption by animals or humans which include respective quantities of flax oil and non-flax carbohydrate. The flax oil and carbohydrate are mixed together and simultaneously subjected to an elevated temperature of at least about 120° F. and subsequently cooled; the flax oil is used at a level so that the final product contains at least about 5% by weight flax oil. It has been found that the products of the invention, when fed at effective levels, induce increased in vivo synthesis of desirable eicosapentaenoic acid (EPA).

35 Claims, 5 Drawing Sheets

OTHER PUBLICATIONS

Calder, P.C.. 1999. Dietary fatty acids and the immune system. Lipids, vol. 34, Supplement S137-S140.

Chang, H. R., D. Arsenijevic, J. C. Pechere, P.F. Piguet, N. Mensi, L. Girardier, and A. G. Dulloo. 1992. Dietary supplementation with fish oils enhances in vivo synthesis of tumor necrosis factor. Immunology Letters 34:13-18.

Chilliard, Y. 1993. Dietary fat and adipose tissue metabolism in ruminants, pigs, and rodents: A Review. J. Dairy Sci. 76(12):3897-3931.

Eiger, Steven M., and M. J. Kluger. 1983. Thermogenesis and fever. In: L. Girardier and M. J. Stock (eds.) Mammalian Thermogenesis. pp. 305-320. Chapman and Hall, Ltd., New York.

Elsasser, Theodore H., N. C. Steele, and R. Fayer. 1995. Cytokines, stress, and growth modulation. In: M. J. Myers and M. P. Murtaugh (eds.) Cytokines in Animal Health and Disease. pp. 261-290. Marcel Dekker, Inc. New York.

Endres, S., R. Ghorbani, V. E. Kelley, K. Georgilis, G. Lonnemann, J. W. M. Vander Meer, J. G. Cannon, T. S. Rogers, M. S. Klempner, P. C. Weber, E. J. Schaefer, S. M. Wolff, and C. A. Dinarello. 1989. The effect of dietary supplementation with n-3 polyunsaturated fatty acids on the synthesis of IL-1 and TNF by mononuclear cells. New England J. Med. 320:265-271.

Engelberts, I., K. Sundram, A. C. Van Houwelingen, G. Hornstra, A. D. Kester, M. Ceska, G. J. Francot, C. J. van der Linden, and W. A. Buurman. 1993. The effect of replacement of dietary fat by palm oil on in vitro cytokine release. British Journal of Nutrition 69(1):159-167.

Grimble, R. F. 1990. Nutrition and cytokine action. Nutrition Research Reviews 3:193-210.

Grimble, R. F. 1994. The modulation of immune function by dietary fat. British Journal of Intensive Care. 4:159-167.

Grimble, R. F. 1998. Dietary lipids and the inflammatory response. Proceedings of the Nutrition Society. 57:535-542.

Kluger, Matthew J. 1980. Fever. Pediatrics 66(5):720-724.

Lee, T. H., R. L. Hoover, J. D. Williams. 1985. Effect of dietary enrichment with eicosapentaenoic and docosahexaenoic acids on in vivo neutrophil and monocyte leukotrienes generation and neutrophil function. The New England Journal of Medicine 312(19):1217-1223.

Limaos, E. A., E. B. Ribeiro, and A. H. Gordon. 1985. Effect of endogenous pyrogen, corticosteroids and inhibitors of prostaglandins and leukotrienes on the plasma concentrations of haptoglobin and fibrinogen in rats. Brazilian J. Med. Biol. Res. 18(4):549-555.

Lokesh, B. R., J. M. Black, and J. E. Kinsella. 1988. The suppression of eicosanoid synthesis of peritoneal macrophages is influenced by the ratio of dietary docosahexaenoic acid to linoleic acid. Lipids 24:589-595.

Lokesh, B. R., T. J. Sayers, and J. E. Kinsella. 1990. Interleukin-1 and tumor necrosis factor synthesis by mouse peritoneal macrophages is enhanced by dietary n-3 polyunsaturated fatty acids. Immunology Letters. 23(4):281-285.

Mascioli, E. A., Y. Iwasa, S. Trimbo, L. Leader, B. R. Bistrian, and G. L. Blackburn. 1989. Endotoxin challenge after menhaden oil diet: effects on survival of guinea pigs. Am. J. Clin. Nutr. 49:277-282.

Mascioli, E., L. Leader, E. Flores, S. Trimbo, B. Bistrian, and B. Blackburn. 1988. Enhanced survival to endotoxin in guinea pigs fed IV fish oil emulsion. Lipids 23(6):623-625.

Miles, E. A., and P. C. Calder. 1998. Modulation of immune function by dietary fatty acids. Proceedings of the Nutrition Society 57:277-292.

McMurchie, E. J., J. A. Rinaldi, S. L. Burnard, G. S. Patten, M. Neumann, G. H. McIntosh, M. Abbey, and R. A. Gibson. 1990. Incorporation and effects of dietary eicosapentaenoate (20:5(n-3)) on plasma and erythrocyte lipids of the marmoset following dietary supplementation with differing levels of linoleic acid. Biochimica et Biophysica Acta. 1045:164-173.

Mulrooney, H. M. And R. F. Grimble. 1993. Influence of butter and of corn, coconut and fish oils on the effects of recombinant human necrosis factor-á in rats. Clinical Science 84:105-112.

Ohtsuka, H., K. Ohki, T. Tanaka, M. Tajima, T. Yoshino, and K. Takahashi. 1997. Circulating tumor necrosis factor and interleukin-1 after administration of LPS in adult cows. J. Vet. Med. Sci. 59(10):927-929.

Palmquist, D. L., and T. C. Jenkins. 1980. Fat in lactation rations: Review. J. Dairy Sci. 63:1-14.

Peterson, L. D., N. M. Jeffery, F. Thies, P. Sanderson, E. A. Newsholme, and P. C. Calder. 1998. Eicosapentaenoic and docosahexaenoic acids alter rat spleen leukocyte fatty acid composition and prostaglandin E2 production but have different effects on lymphocyte functions and cell-mediated immunity. Lipids 33(2):171-180.

Pomposelli, J. J., E. A. Mascioli, B. R. Bistrian, S. M. Lopes, G. L. Blackburn. 1989. Attenuation of the febrile response in guinea pigs by fish oil enriched diets. Journal of Parenteral and Enteral Nutrition 13(2):136-140.

Schrijver, R. D., D. Vermeulen, and E. Viaene. 1991. Lipid metabolism responses in rats fed beef tallow, native or randomized fish oil and native or randomized peanut oil. J. Nutr. 121:948-955.

Wigmore, S. J., K. C. H. Fearon, J. P. Maingay, and J. A. Ross. 1997. Down-regulation of the acute-phase response in patients with pancreatic cancer cachexia receiving oral eicosapentaenoic acid is mediated via suppression of interleukin-6. Clinical Science 92:215-221.

Yagoob, P. and P. C. Calder. 1995. Effects of dietary lipid manipulation upon inflammatory mediator production by murine macrophages. Cellular Immunology 163:120-128.

* cited by examiner

PRODUCT AND PROCESS FOR ELEVATING LIPID BLOOD LEVELS IN LIVESTOCK

BACKGROUND OF THE INVENTION

1. Field of the Invention

The present invention is broadly concerned with improved feed or food products, (e.g., solid feed supplement blocks or flowable top dressings) which can be fed to animals or humans in order to induce a significant increase in eicosapentaenoic acid (EPA) in the blood plasma of the animals or humans. The invention also is directed to corresponding methods of feeding and to processes for preparing the improved feed or food products.

2. Description of the Prior Art

Much interest has focused on dietary fat and its effect in modulating mammalian immune and inflammatory responses during infection or disease. Dietary lipids affect the immune system in several disease models of rodents and humans. Because dietary fat can alter cell membrane composition, it is a major modulator of immune function (Grimble, 1994; Miles and Calder, 1998). Possible mechanisms include impacting the amount and type of lipid-derived inflammatory mediators (eicosanoids) and inhibiting over-production of certain cytokines produced by cells of the immune system (Calder, 1996).

Eicosanoids are a family of oxygenated derivatives of polyunsaturated fatty acids (PUFA). Two of the omega-6 (n-6) PUFA [arachidonic acid (AA) and dihomo-gamma-linolenic acids] and one omega-3 (n-3) PUFA [eicosapentaenoic acid (EPA)] act as precursors for eicosanoids. These PUFA, as part of the cellular membrane phospholipid, can influence synthesis of eicosanoids such as prostaglandins (PG) and leukotrienes (LT), and platelet activating factor (Miles and Calder, 1998; Calder, 1997; Grimble 1994). Linoleic acid, an n-6 PUFA, is converted to AA in animal cells. In contrast, linolenic acid, an n-3 PUFA, is converted to EPA in animal cells. Whereas AA is a precursor compound to the 2-series PG and the 4-series LT, EPA is a precursor to the 3 and 5-series PG and LT, respectively (Calder, 1997; Grimble 1998). The 2-series PG and 4-series LT are more pro-inflammatory than the 3-series PG and 5-series LT (Calder, 1997; Grimble 1994).

Mulrooney and Grimble (1993) found that feeding butter, fish, and coconut oils, all of which contain low levels of n-6 PUFA, reduced the anorexic effect caused by an intraperitoneal injection of rats with TNF-alpha. In contrast, hepatic and lung protein synthesis, anorexia, and body weight loss were amplified in response to endotoxin injection when dietary n-6 PUFA intake was increased by feeding corn oil compared to feeding butter or olive oil (Besler and Grimble, 1995).

In accordance with these findings, Mascioli et al. (1988; 1989) found that administering guinea pigs fish oil (rich in n-3 PUFA) significantly improved survival after endotoxin infusion compared to animals fed safflower oil. In addition, Pomposelli et al. (1989) observed a reduced interleukin-1 febrile response in guinea pigs fed fish oil compared to those fed safflower oil. These authors conclude that dietary fat can potentially have profound effects on the host animal's response to toxic insults that result in injury and(or) infection.

Cytokines are soluble protein mediators produced by immune cells following activation with stimuli such as infectious diseases. Cytokines play an important role in modulating activity of the immune system and in increasing lipolysis, gluconeogenesis, and muscle proteolysis. The result is provision of substrates for use by the immune system and for acute-phase protein synthesis (Grimble, 1990). While actions of cytokines can be beneficial, excessive or inappropriate production can lead to tissue damage, which occurs in a number of inflammatory diseases (Elsasser et al., 1995). Cytokine production by immune cells is regulated by eicosanoids; since dietary lipids affect eicosanoid production, they also impact cytokine production (Calder, 1998b).

Diets which promote the in vivo synthesis of EPA are known to ameliorate harmful effects of an over-exaggerated, disproportionate inflammatory and immune responses. Accordingly, there is a need in the art for improved animal feeds or human foods which contain fatty acids such as ALA in a form that will enhance and amplify conversion to EPA.

SUMMARY OF THE INVENTION

The present invention provides improved feed or food products for ingestion by animals or humans and which provide ALA in a form which yields exceptionally high quantities of desirable EPA in the animal or human. Broadly speaking, the feed or food products of the invention comprise a mixture including respective quantities of flax oil and a non-flax carbohydrate, the flax oil and non-flax carbohydrate having been mixed together and simultaneously subjected to an elevated temperature of at least about 120° F. and subsequently cooled, the flax oil being present in the product at a level of at least about 5% by weight (more preferably at least about 10% by weight). The product may be in the form of a cast, solid block or alternately may be a flowable product such as a liquid feed dressing.

Preferably, the flax oil component should be derived from liquid flax oil, flax seed, free fatty acid mixtures, fatty acid soaps, flax oil-containing derivatives of any of the foregoing, and mixtures thereof. Normally, flax oil and milled flax seed are used, especially when solid block feed supplements are prepared. The non-flax carbohydrate component is advantageously selected from the group consisting of carbohydrate-containing syrups, sugars, starches, and mixtures thereof. Cane and beet molasses, concentrated separator by-product, corn steep liquor, soybean molasses, and whey are suitable sources for acceptable non-flax carbohydrates.

The feed or food products of the invention also normally contain respective quantities of protein, fat, and fiber. Protein may be present at a level of from about 5-40% by weight, and more preferably from about 10-25% by weight. The protein fraction may be derived from a wide variety of sources, e.g., plant-derived proteins such as soybean meal, concentrate or isolate, canola meal, sunflower meal, linseed meal, safflower meal, corn gluten meal, cottonseed meal, or animal-derived proteins such as blood meal, feather meal, and whey. The fat should be present at a level of from about 5-35% by weight, more preferably from about 10-20% by weight. Fat sources include flax or flax derivatives, canola and canola derivatives, soybean oil, fish oil, fish meal, and marine algae. The fiber should be present at a level of from about 0.25-10% by weight, more preferably from about 0.5-3% by weight.

When solid feed supplement blocks are produced in accordance with the invention, they should have a density of from about 50-70 lbs/cu. ft., and also preferably should have deliquescent properties.

It has been discovered that the feed or food products of the invention, when fed in effective amounts to humans or animals, yields unexpectedly high increases in plasma EPA. The invention is particularly suited for feeding to domesticated animals, such as bovine, ovine, equine, porcine, and caprine animals. However, it is believed that good effects will be obtained when feeding poultry and other non-mammalian species. Generally speaking, the products should be fed at a level to provide a flax oil content of at least about 1.5 grams per kilogram of body weight of the animal or human, and more preferably at least about 5 grams per kilogram of body weight of the animal or human. In order to obtain a desirable result, the products of the invention should be fed at a level to increase the plasma EPA concentration of said animal or human by at least about 10% (more preferably at least about 25%) as compared with the plasma EPA concentration of the animal or human prior to feeding of the product.

Methods for preparing feed or food products pursuant to the invention involve first preparing a mixture comprising flax oil and non-flax carbohydrate, and subjecting the mixture to an elevated temperature of at least about 120° F. Thereupon, the heated mixture is cooled and the final feed or food product is formed. Such processing may involve cooling to ambient temperature, extrusion processing, expansion, or pelleting.

Particularly preferred methods for producing solid products involve continuous processing techniques of the type described in U.S. Pat. No. 5,482,729 and pending U.S. patent application Ser. No. 10/205,857 filed Jul. 26, 2002, both incorporated by reference herein. These methods are carried out by first mixing together respective quantities of flax oil and non-flax carbohydrate, followed by indirect heating in a shell and tube heat exchanger to a temperature of from about 275-400° F. (more preferably from about 300-3500° F.). The output from the heat exchanger may be passed in serial order through a cyclone and vacuum chamber in order to dewater the mixture, or it can be further heat-processed before vacuumization. Next, dry ingredients including milled flax seed are added to the mixture and blended to homogeneity before the final processing steps towards formation of the solid product.

DETAILED DESCRIPTION OF THE PREFERRED EMBODIMENTS

Figure 1:
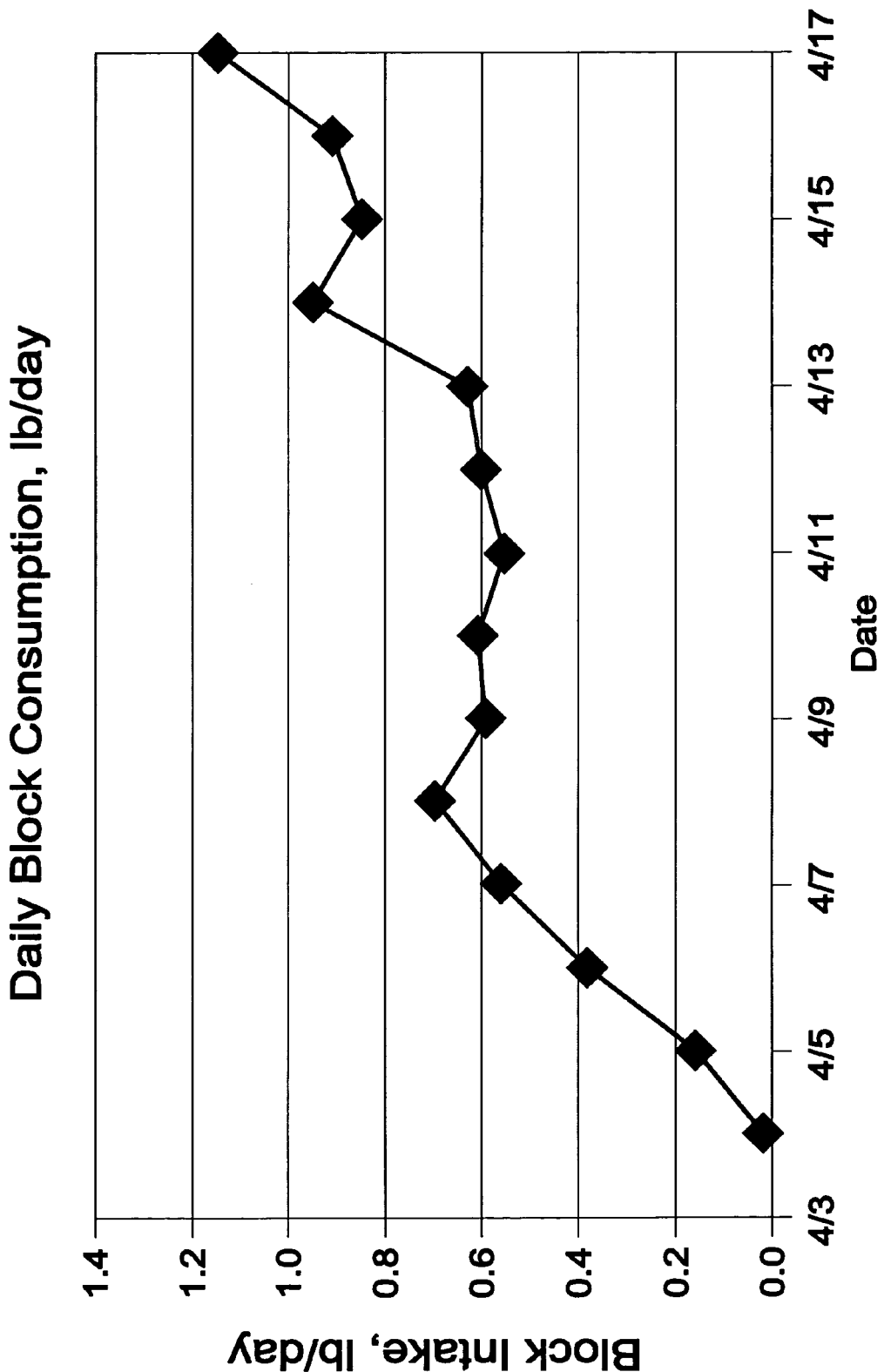
FIG. 1 is a graph illustrating the consumption of feed blocks in accordance with the invention during 14 days of the study described in Example 4.

The following examples set forth preferred processes for the preparation of solid feed blocks in accordance with the invention, as well as data confirming the unique characteristics of the block products. It is to be understood that these examples are provided by way of illustration only, and nothing therein should be taken as a limitation upon the overall scope of the invention.

EXAMPLE 1

One preferred method for producing the feed blocks of the invention utilizes the equipment and general process scheme described in U.S. Pat. No. 5,482,729, incorporated by reference herein. Broadly speaking, the method and apparatus are designed for continuous production of final product and make use of a blender for blending starting ingredients including molasses, vegetable fat, and flax oil. The blender is coupled with an oil-heated shell and tube heat exchanger for heating the blended ingredients to a desired temperature. The heated ingredients then pass in serial order through a cyclone and a vacuum tank to dewater the heated ingredients. Next, dry ingredients including flax seed are mixed with the dewatered and heated ingredients in a screw mixer to create a homogeneous, flowable product. This product is then partially cooled and deposited in block containers for final cooling and to create the solid block product.

In more detail, 1,603 lbs of beet molasses are continuously blended with 118 lbs of edible flax seed oil in a conventional blender, and the blended mixture is then directed to an oil-heated shell and tube heat exchanger. During passage through the exchanger, the molasses/flax seed oil mixture is heated to a temperature of about 338° F., whereupon the heated mixture is directed in serial order through a cyclone and a vacuum tank, the latter being equipped with a vacuum pump in order to create vacuum conditions on the order of 21-24 inches of mercury within the vacuum tank. This causes a release of steam and moisture from the mixture, so that the mixture leaving the vacuum tank has no more than about 5% by weight moisture (more preferably the moisture level should be less than about 2% by weight). The heated and dewatered mixture is then fed to a screw mixer along with 600 lbs dry ingredients. These ingredients include corn gluten meal (38 lbs), milled and cracked flax seed (440 lbs), mineral mixture (120 lbs) made up of calcium phosphate, limestone, and trace minerals, and vitamin premixes (2 lbs). The mixture exiting the screw mixer has a temperature on the order of 190° F. and is highly viscous. This mixture is deposited on an elongated cooling belt for partial cooling to a temperature of around 130-140° F. At the end of the cooling belt, the mixture is deposited into individual block-forming containers, and is allowed to fully cool therein to ambient temperature, thereby forming the desired solid block product.

EXAMPLE 2

The apparatus and method of Example 1 was also used to prepare solid feed blocks having somewhat different starting ingredients. In particular, 1,403 lbs of cane molasses was used in lieu of the beet molasses, and the amount of edible flax seed oil was increased to 195 lbs. The dry ingredients totaled 640 lbs, made up of 252 lbs of milled flax seed, 290 of cottonseed meal, 88 lbs of a mineral mixture (made up of calcium phosphate, limestone, and trace minerals), and vitamin premixes totaling 10 lbs.

EXAMPLE 3

In this example, a modified process was employed to produce the flax-supplemented feed blocks of the invention, as described in pending application for U.S. Letters Patent Ser. No. 10/205,857 filed Jul. 26, 2002, and incorporated by reference herein. In this process, the shell and tube heat exchanger described in Examples 1 and 2 are used as a preheater and a series of parallel batch atmospheric pressure final heaters are downstream of the preheater and upstream of the vacuum tank (the use of a cyclone is eliminated). The parallel final heaters are arranged and have sufficient capacity to maintain the continuity of the process. Thus, the output from the shell and tube exchanger is directed to one of the final heaters while previously received product is being processed and/or delivered in the remaining final heaters. Such two-stage heating increases the capacity of the system without disrupting desirable continuous operation.

The ingredients of Examples 1 and 2 can be used with this modified process, and the only significant difference is that the material exiting the heat exchanger is directed to the parallel final heaters as described. The mixture leaving the respective final heaters is typically at a temperature of about 250-280° F.

EXAMPLE 4

In this example, a comparative study over 28 days was conducted to determine the in vivo production of EPA consuming ad libitum the processed feed blocks of the invention versus the same quantities of unprocessed ingredients of those blocks. A negative control also formed a part of the study.

In detail, 30 randomly selected cross-bred beef heifers (average weight 575 lbs) were placed into 3 groups of 10 animals per group. The negative control group was fed ad libitum a basal diet consisting of 46% steam-flaked corn, 41.4% alfalfa hay, 8% corn steep liquor, and 4.6% mineral vitamin feed additive supplement (all percentages by weight). The block-fed group was fed the above basal ad libitum diet and allowed to consume ad libitum the blocks produced as described in Example 1. FIG. 1 illustrates the average daily consumption of the blocks by the block-fed group. The positive control group animals were paired with the animals of the block-fed group. At approximately 7:00 a.m. of each day during the study, the amount of block consumed by each animal of the block-fed group during the preceding 24-hour period was measured, and the amounts of flax oil, flax seed, and other dry ingredients were calculated. Approximately one hour later, each paired positive control animal was fed unprocessed flax oil, flax seed, and other dry ingredients in amounts equivalent to the amounts of those ingredients consumed during the preceding 24-hour period by the corresponding animal from the block-fed group.

Figure 2:
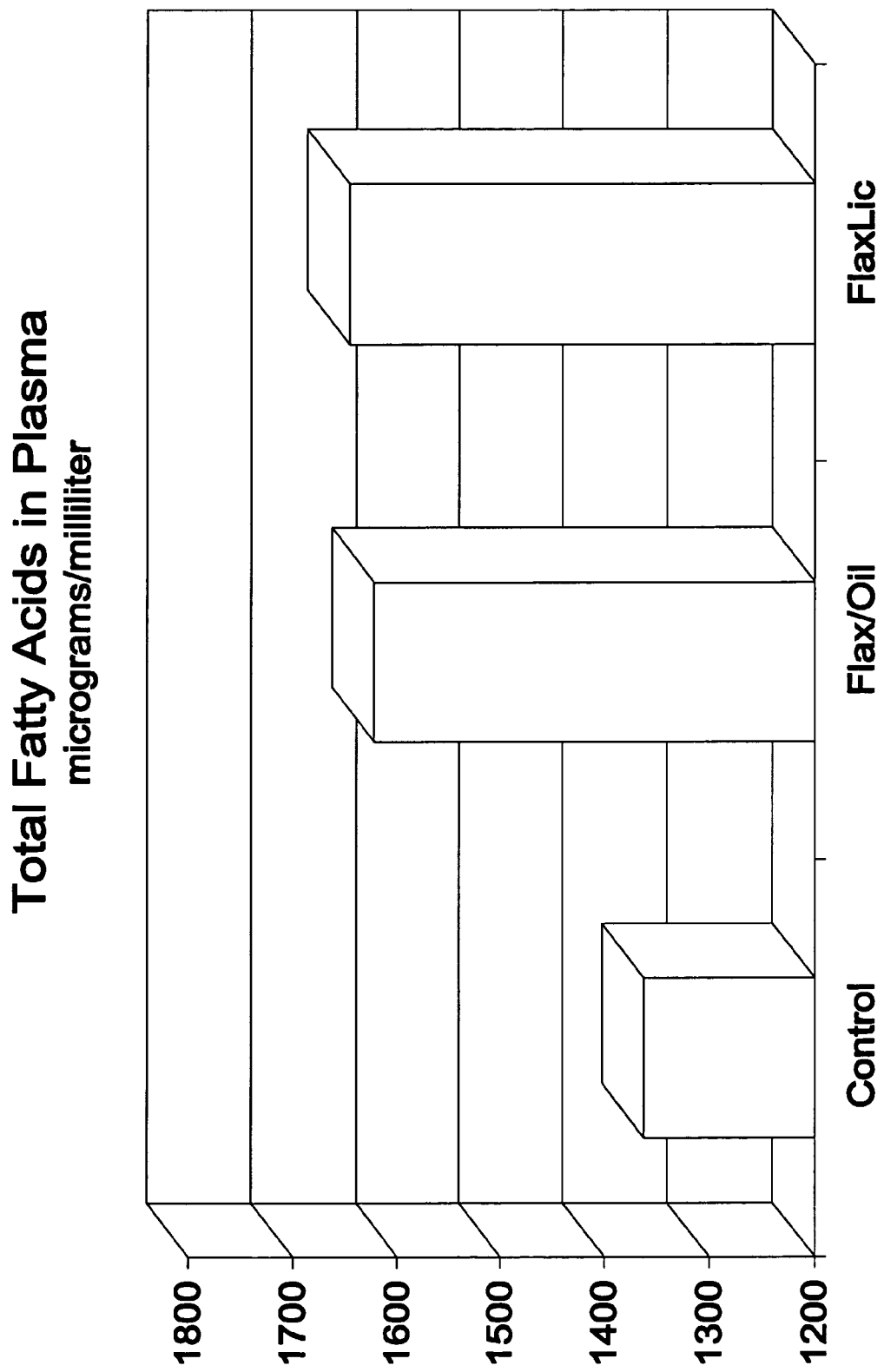
FIG. 2 is a comparative graph depicting the total average plasma fatty acid content for the three test groups described in Example 4, namely the negative control group, the group fed unprocessed block ingredients (labeled "flax/oil"), and the group fed the preferred blocks of the invention (labeled "FlaxLic")
Figure 3:
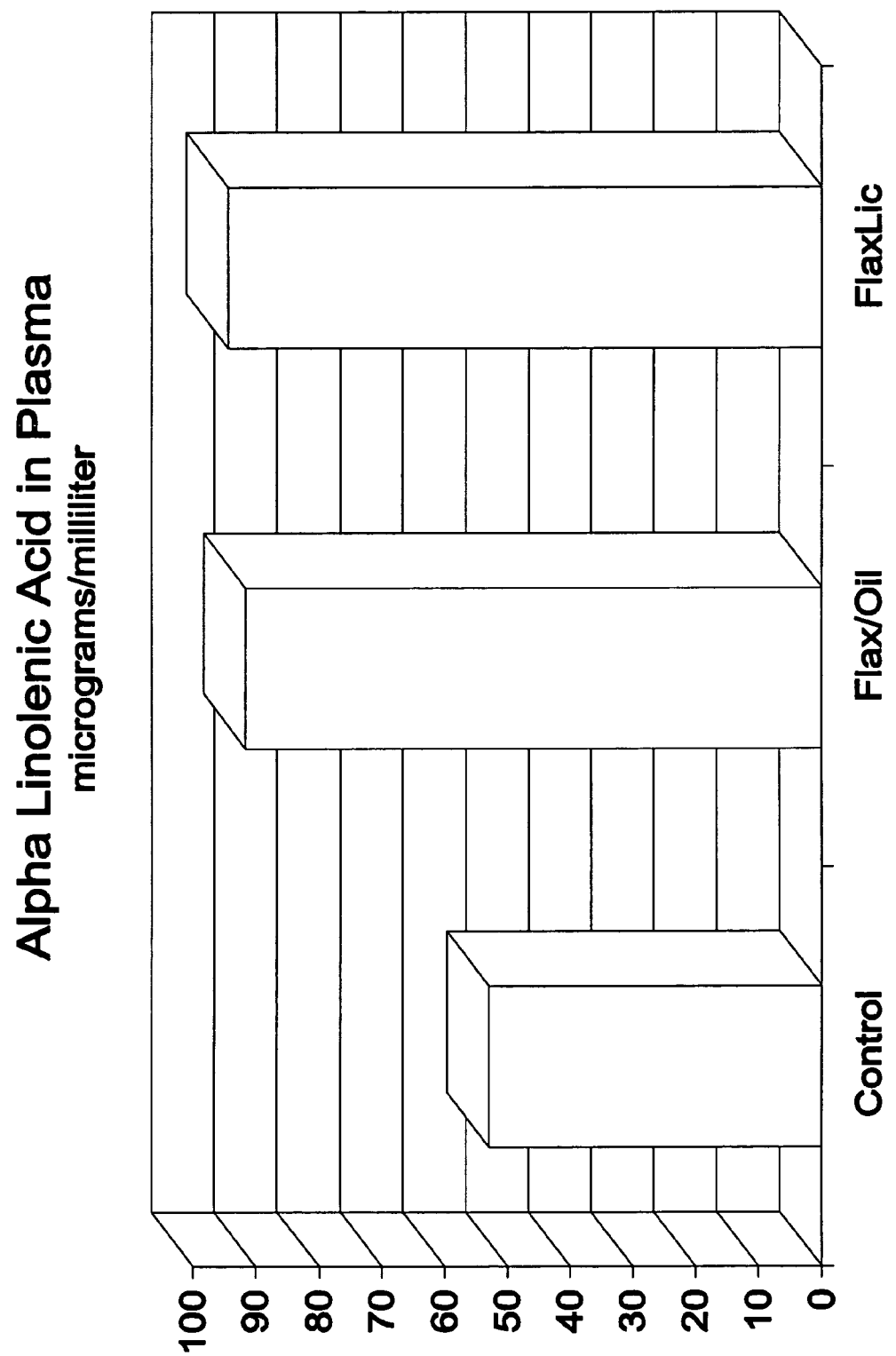
FIG. 3 is a comparative graph depicting the average total plasma ALA content for each of the three test groups described in Example 4.
Figure 4:
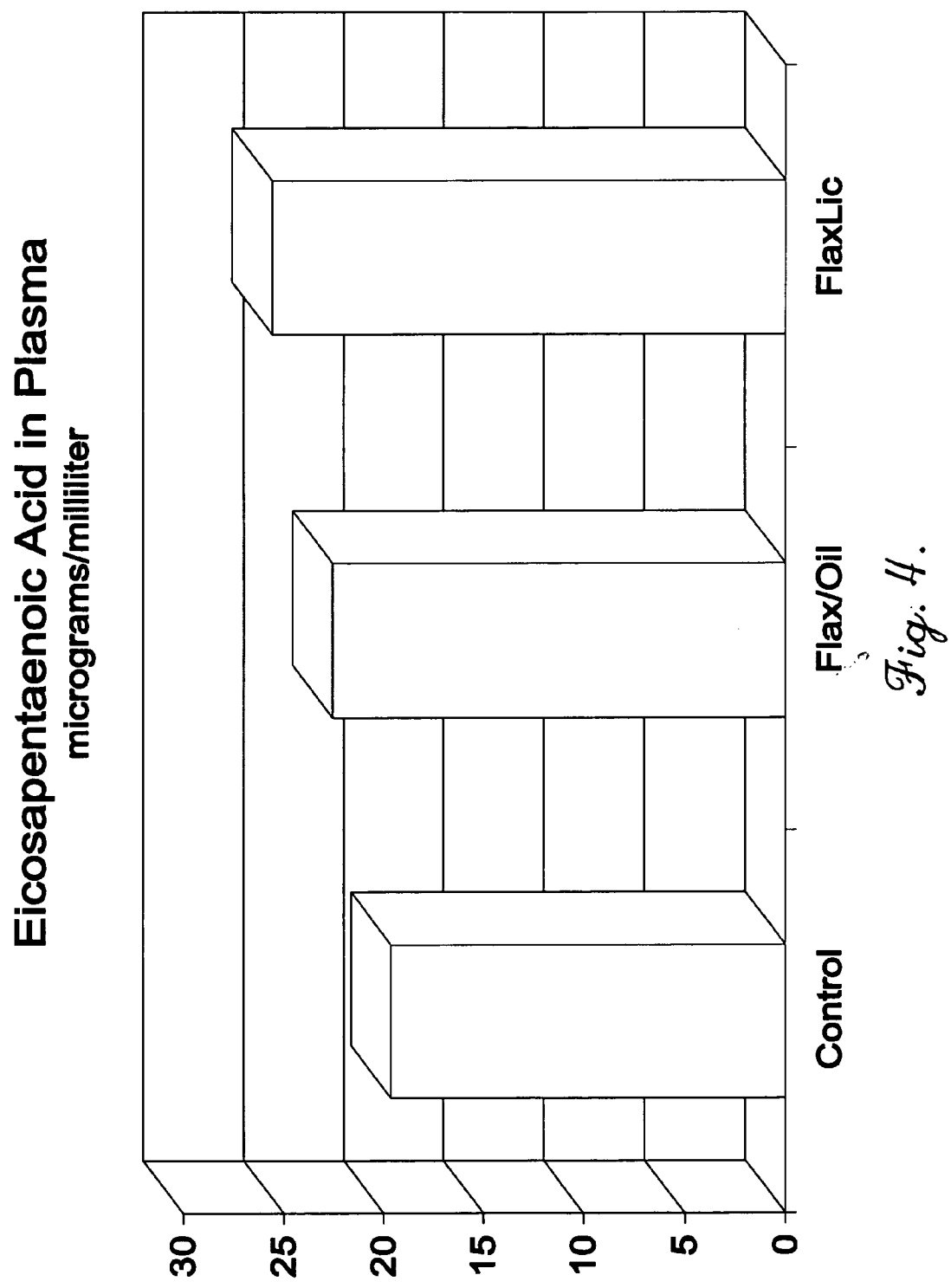
FIG. 4 is a comparative graph depicting the total average EPA content for the three test groups described in Example 4.
Figure 5:
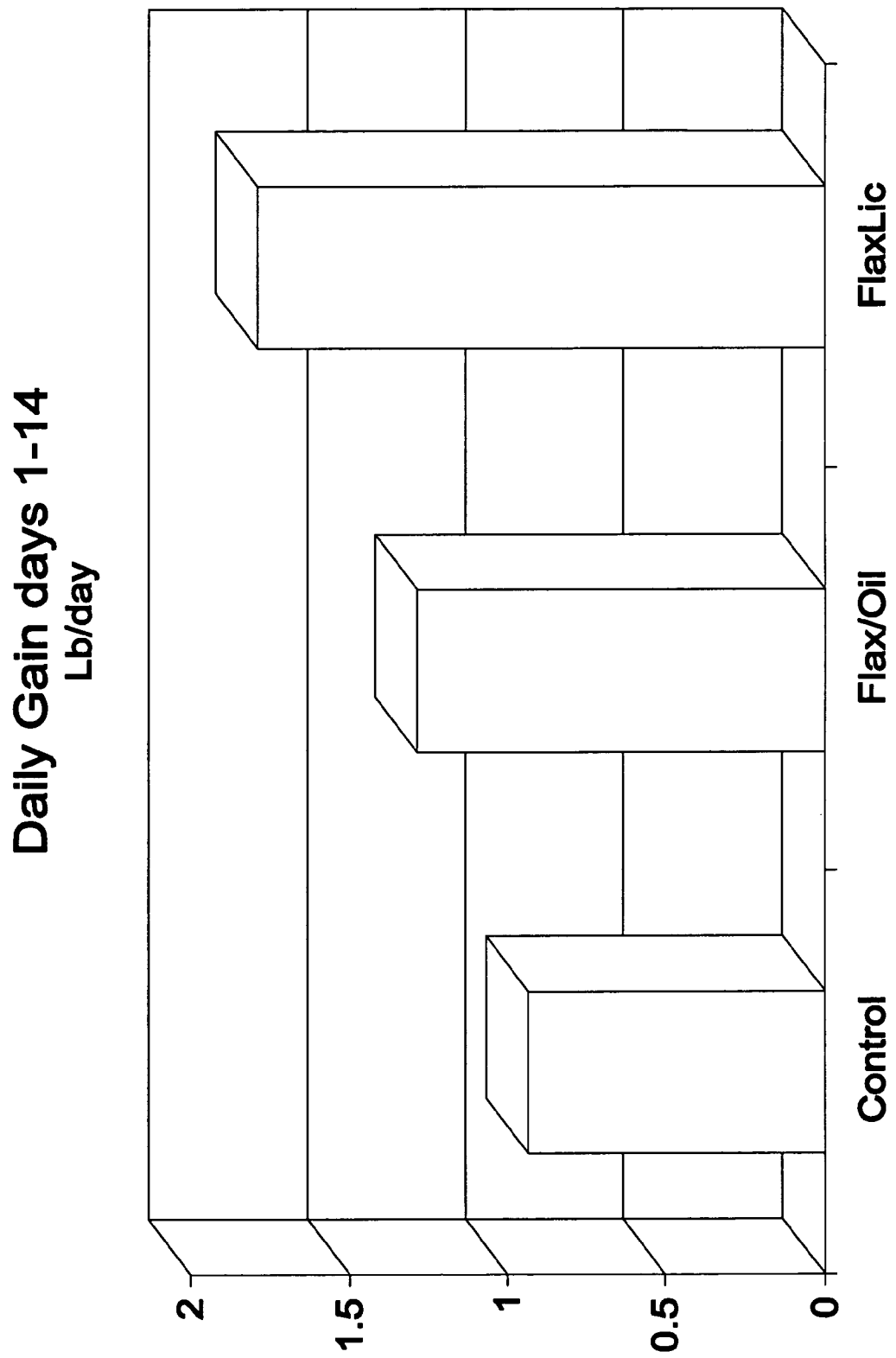
FIG. 5 is a comparative graph depicting the average daily weight gain for the cattle of the three test groups described in Example 4.

At 0 and 21 days, a blood sample was drawn via jugular puncture from each of the 30 animals, and plasma was derived from each blood sample. Fatty acid profiles were determined from each plasma sample, namely a total fatty acid content and concentrations of ALA and EPA. FIG. 2 is a graph setting forth the average total fatty acid content for the three groups at day 21. FIG. 3 is a similar graph setting forth the average ALA content for the three groups at day 21. FIG. 4 is a graph setting forth the average EPA content for the three groups at day 21. Finally, FIG. 5 is a graph depicting the average daily weight gain for the three groups through days 1-14 of the study.

As can be seen from a study of FIG. 2, the comparative total fatty acid contents between the block-fed FlaxLic group and the positive control flax seed/flax oil group were essentially the same, without any statistically significant difference. However, there was a statistically significant increase in total fatty acid content between the negative control group and the other groups.

Similarly, FIG. 3 illustrates that the average ALA content of the plasma samples was essentially the same between the flax seed/flax oil and FlaxLic groups, whereas these levels were elevated as compared with the negative control group.

FIG. 4 depicts the EPA contents of the plasma samples from the three groups. Unexpectedly, the average EPA content for the FlaxLic block-fed group was statistically significantly higher (P<0.01) than for the flax seed/flax oil group fed only equivalent amounts of unprocessed ingredients. Accordingly, it is believed that the intimate admixture of the flax component(s) (e.g., flax oil and/or flax seed) with the molasses under elevated temperature conditions is an important aspect of the invention, and that such results in a beneficial reaction which accounts for the higher average blood plasma EPA content for the FlaxLic group.

FIG. 5 illustrates that the flax seed/flax oil and FlaxLic groups had numerically higher weight gains during days 1-14 of the study, as compared with the negative control (P<0.01). Moreover, there was a significant difference between the early gain performance of the FlaxLic group versus the negative control group (P<0.10), but the difference between the negative control group and flax seed/flax oil group was not statistically significant. This effect diminished during further testing, but such an early-weight gain characteristic at the outset of block feeding may be important in certain feeding contexts.

EXAMPLE 5

A particularly preferred solid feed supplement designed for ad libitum feeding to all classes of beef and dairy cattle was prepared using the method of Example 1. This solid product was prepared as 250 lb blocks and contained a guaranteed nutrient analysis as follows:

| | |
|---|---|
| Crude Protein, minimum | 12.0% |
| Crude Fat, minimum | 15.0% |
| Crude Fiber, minimum | 2.0% |
| ADF, maximum | 2.5% |
| Calcium, minimum | 1.0% |
| Calcium, maximum | 1.5% |
| Phosphorous, minimum | 1.0% |
| Potassium, minimum | 2.5% |
| Cobalt, minimum | 3.0 ppm |
| Copper, minimum | 300 ppm |
| Iodine, minimum | 15 ppm |
| Manganese, minimum | 1,200 ppm |
| Selenuim, minimum | 6.6 ppm |
| Zinc, minimum | 1,200 ppm |
| Vitamin A, minimum | 80,000 IU/lb |
| Vitamin D, minimum | 8,000 IU/lb |
| Vitamin E, minimum | 80 IU/lb |

Preferably, the supplement is provided free-choice to cattle, at the rate of one block for each 15-25 head of cattle. The blocks are placed a minimum of two blocks in each pen or pasture near areas frequented by cattle, such as watering locations, or shade or loafing areas. Cattle normally consume approximately three-quarter pounds per head per day. Consumption may vary depending on climate, grazing conditions, condition of the cattle and/or availability of other feeds. In situations where climate and/or other factors result in consumption less than three-quarter pound per head per day, intake of the supplement can be increased slightly by providing additional blocks in each pen or pasture. It is desirable to also provide access to fresh water and free-choice salt at all times.

LITERATURE REFERENCES

Barber, M. D., J. A. Ross, T. Preston, A. Shenkin, and K. C. H. Fearon. 1999. Fish oil-enriched nutritional supplement attenuates progression of the acute-phase response in weight-losing patients with advanced pancreatic cancer. J. Nutr. 129:1120-1125.

Besler, H. T., and R. F. Grimble. 1995. Comparison of the modulatory influence of maize and olive oils and butter on metabolic responses to endotoxin in rats. Clin. Sci. 88:59-66.

Blatteis, C. M., J. R. Hales, A. A. Fawcett, and T. A. Mashburn Jr. 1988. Fever and regional blood flows in wethers and parturient ewes. J. Appl. Physiol. 65(1):165-172

Calder, P. C. 1996. Immunomodulatory and anti-inflammatory effects of n-3 polyunsaturated fatty acids. Proc. Nutr. Soc. 55:737-774.

Calder, P. C. 1997. n-3 polyunsaturated fatty acids and cytokine production in health and disease. Ann. Nutr. Metab. 41:203-234.

Calder, P. C. 1998a. Fat chance of immunomodulation. Immunol. Today 19(6):244-247.

Calder, P. C. 1998b. Dietary fatty acids and the immune system. Nutr. Reviews 56(1):(II)S70-S83.

Chang, H. R., D. Arsenijevic, J. C. Pechere, P. F. Piguet, N. Mensi, L. Girardier, and A. G. Dulloo. 1992. Dietary supplementation with fish oils enhances in vivo synthesis of tumor necrosis factor. Immunol. Letts. 34:13-18.

Chilliard, Y. 1993. Dietary fat and adipose tissue metabolism in ruminants, pigs, and rodents: A review. J. Dairy Sci. 76(12):3897-3931.

Eiger, S. M., and M. J. Kluger. 1983. Thermogenesis and fever. In: L. Girardier and M. J. Stock (eds.) Mammalian Thermogenesis. pp 305-320. Chapman and Hall, Ltd., New York.

Elsasser, T. H., N. C. Steele, and R. Fayer. 1995. Cytokines, stress, and growth modulation. In: M. J. Myers and M. P. Murtaugh (eds.) Cytokines in Animal Health and Disease. pp. 261-290. Marcel Dekker, Inc. New York.

Endres, S., R. Ghorbani, V. E. Kelley, K. Georgilis, G. Lonnemann, J. W. M. Vander Meer, J. G. Cannon, T. S. Rogers, M. S. Klempner, P. C. Weber, E. J. Schaefer, S. M. Wolff, and C. A. Dinarello. 1989. The effect of dietary supplementation with n-3 polyunsaturated fatty acids on the synthesis of IL-1 and TNF by mononuclear cells. New England J. Med. 320:265-271.

Engelberts, I., K. Sundram, A. C. Van Houwelingen, G. Homstra, A. D. Kester, M. Ceska, G. J. Francot, C. J. van der Linden, and W. A. Buurman. 1993. The effect of replacement of dietary fat by palm oil on in vitro cytokine release. Br. J. Nutr. 69(1):159-167.

Grimble, R. F. 1990. Nutrition and cytokine action. Nutr. Res. Rev. 3:193-210.

Grimble, R. F. 1994. The modulation of immune function by dietary fat. Brit. J. Intensive Care. 4:159-167.

Grimble, R. F. 1998. Dietary lipids and the inflammatory response. Proc. Nutr. Soc. 57:535-542.

Kluger, M. J. 1980. Fever. Pediatrics 66(5):720-724.

Lee, T. H., R. L. Hoover, J. D. Williams. 1985. Effect of dietary enrichment with eicosapentaenoic and docosahexaenoic acids on in vivo neutrophil and monocyte leukotrienes generation and neutrophil function. N. Eng. J. Med. 312(19): 1217-1223.

Limaos, E. A., E. B. Ribeiro, and A. H. Gordon. 1985. Effect of endogenous pyrogen, corticosteroids and inhibitors of prostaglandins and leukotrienes on the plasma concentrations of haptoglobin and fibrinogen in rats. Braz. J. Med. Biol. Res. 18(4):549-555.

Lokesh, B. R., J. M. Black, and J. E. Kinsella. 1988. The suppression of eicosanoid synthesis of peritoneal macrophages is influenced by the ratio of dietary linoleic to docosahexaenoic acid. Lipids 24:589-595.

Lokesh, B. R., T. J. Sayers, and J. E. Kinsella. 1990. Interleukin-1 and tumor necrosis factor synthesis by mouse peritoneal macrophages is enhanced by dietary n-3 polyunsaturated fatty acids. Immunol. Lett. 23(4):281-285.

Mascioli, E. A., Y. Iwasa, S. Trimbo, L. Leader, B. R. Bistrian, and G. L. Blackburn. 1989. Endotoxin challenge after menhaden oil diet: effects on survival of guinea pigs. Am. J. Clin. Nutr. 49:277-282.

Mascioli, E., L. Leader, E. Flores, S. Trimbo, B. Bistrian, and B. Blackburn. 1988. Enhanced survival to endotoxin in guinea pigs fed IV fish oil emulsion. Lipids 23(6):623-625.

Miles, E. A., and P. C. Calder. 1998. Modulation of immune function by dietary fatty acids. Proc. Nutr. Soc. 57:277-292.

McMurchie, E. J., J. A. Rinaldi, S. L. Burnard, G. S. Patten, M. Neumann, G. H. McIntosh, M. Abbey, and R. A. Gibson. 1990. Incorporation and effects of dietary eicosapentaenoate (20:5(n-3)) on plasma and erythrocyte lipids of the marmoset following dietary supplementation with differing levels of linoleic acid. Biochimica et Biophysica Acta. 1045:164-173.

Mulrooney, H. M. and R. F. Grimble. 1993. Influence of butter and of corn, coconut and fish oils on the effects of recombinant human necrosis factor-á in rats. Clin. Sci. 84:105-112.

Ohtsuka, H, K. Ohki, T. Tanaka, M. Tajima, T. Yoshino, and K. Takahashi. 1997. Circulating tumor necrosis factor and interleukin-1 after administration of LPS in adult cows. J. Vet. Med. Sci. 59(10):927-929.

Palmquist, D. L., and T. C. Jenkins. 1980. Fat in lactation rations: Review. J. Dairy Sci. 63:1-14.

Peterson, L. D., N. M. Jeffery, F. Thies, P. Sanderson, E. A. Newsholme, and P. C. Calder. 1998. Eicosapentaenoic and docosahexaenoic acids alter rat spleen leukocyte fatty acid composition and prostaglandin E2 production but have different effects on lymphocyte functions and cell-mediated immunity. Lipids 33(2):171-180.

Pomposelli, J. J., E. A. Mascioli, B. R. Bistrian, S. M. Lopes, G. L. Blackburn. 1989. Attenuation of the febrile response in guinea pigs by fish oil enriched diets. J. Parenter. and Enteral Nutr. 13(2):136-140.

Schrijver, R. D., D. Vermeulen, and E. Viaene. 1991. Lipid metabolism responses in rats fed beef tallow, native or randomized fish oil and native or randomized peanut oil. J. Nutr. 121:948-955.

Wigmore, S. J., K. C. H. Fearon, J. P. Maingay, and J. A. Ross. 1997. Down-regulation of the acute-phase response in patients with pancreatic cancer cachexia receiving oral eicosapentaenoic acid is mediated via suppression of interleukin-6. Clin. Sci. 92:215-221.

Yaqoob, P. and P. C. Calder. 1995. Effects of dietary lipid manipulation upon inflammatory mediator production by murine macrophages. Cell Immunol. 163:120-128.

I claim:

1. A feed product designed for consumption by an animal selected from the group consisting of bovine, ovine, and caprine animals, said feed product comprising a mixture including flax oil, flax seed, and a non-flax carbohydrate, said flax oil and non-flax carbohydrate having been mixed together and simultaneously subjected to an elevated temperature of at least about 120° F. through use of a heater to supply heat to the mixture and subsequently cooled, the flax oil content of said feed or food product derived from said flax oil and said flax seed being at a level of at least about 10% by weight, said product also including protein, fiber, and fat different from said flax oil, said feed product operable to elevate the plasma EPA concentration of said animal by at least about 10%, as compared with the plasma EPA concentration of the animal prior to feeding of the feed product.

2. The product of claim 1, said product being in the form of a cast, solid block.

3. The product of claim 1, said product being in the form of a flowable product.

4. The product of claim 1, said product also including flax oil derived from free fatty acid mixtures, fatty acid soaps, flax oil-containing derivatives of any of the foregoing, and mixtures thereof.

5. The product of claim 1, said non-flax carbohydrate selected from the group consisting of carbohydrate-containing syrups, sugars, starches, and mixtures thereof.

6. The product of claim 1, said protein being present at a level of from about 5-40% by weight.

7. The product of claim 6, said level being from about 10-25% by weight.

8. The product of claim 1, said fat being present at a level of from about 5-35% by weight.

9. The product of claim 8, said level being from about 10-20% by weight.

10. The product of claim 1, said fiber being present at a level of from about 0.25-10% by weight.

11. The product of claim 10, said level being from about 0.5-3% by weight.

12. The product of claim 1, said product including vitamins and minerals.

13. The product of claim 1, said product being in the form of a solid block having a density of from about 50-70 lbs/cu. ft.

14. The product of claim 1, said product being in the form of a solid block, said block having deliquescent properties.

15. A method of preparing a feed product designed for feeding to an animal selected from the group consisting of bovine, ovine, and caprine animals, said method comprising the steps of:
preparing a mixture comprising flax oil, flax seed, a fat different from said flax oil, and non-flax carbohydrate;
subjecting said mixture to an elevated temperature of at least about 120° F. through use of a heater to supply heat to the mixture; and
cooling said supplemented mixture and forming said feed product, said feed having a flax oil content derived from said flax oil and flax seed of at least about 10% by weight,
said feed product operable to elevate the plasma EPA concentration of said animal by at least about 10%, as compared with the plasma EPA concentration of the animal prior to feeding of the feed product.

16. The method of claim 15, including the step of cooling said heated mixture to form a cast, solid block.

17. The method of claim 15, including the step of cooling said mixture to form a flowable product.

18. The method of claim 15, said product also including flax oil derived from free fatty acid mixtures, fatty acid soaps, flax oil-containing derivatives of any of the foregoing, and mixtures thereof.

19. The method of claim 15, said non-flax carbohydrate selected from the group consisting of carbohydrate-containing syrups, sugars, starches, and mixtures thereof.

20. The method of claim 15, said protein being present in said feed or food at a level of from about 5-40% by weight.

21. The method of claim 20, said level being from about 10-25% by weight.

22. The method of claim 15, said fat being present in said feed or food at a level of from about 5-35% by weight.

23. The method of claim 22, said level being from about 10-20% by weight.

24. The method of claim 15, said fiber being present in said feed or food at a level of from about 0.25-10% by weight.

25. The method of claim 24, said level being from about 0.5-3% by weight.

26. The method of claim 15, said feed or food including vitamins and minerals.

27. The method of claim 15, said feed or food being in the form of a solid block having a density of from about 50-70 lbs/cu, ft.

28. The method of claim 15, said feed or food being in the form of a solid block, said block having deliquescent properties.

29. The method of claim 15, the weight amount of said non-flax carbohydrate in said mixture being greater than the weight amount of said flax oil therein.

30. The method of claim 15, including the step of heating said mixture using a heat exchanger.

31. The method of claim 15, said heater-supplied heat being the only source of heat for said mixture.

32. The method of claim 15, said temperature being from about 275-400° F.

33. The product of claim 1, said flax oil and non-flax carbohydrate having been heated using a heat exchanger.

34. The product of claim 1, said heater-supplied heat being the only source of heat for said mixture.

35. The product of claim 1, said temperature being from about 275-400° F.

* * * * *